United States Patent
Genosar

(10) Patent No.: US 11,001,435 B2
(45) Date of Patent: May 11, 2021

(54) PRESSURE CARTRIDGE AND ACTIVATION MECHANISM

(71) Applicant: AKTIVAX, INC., Broomfield, CO (US)

(72) Inventor: Amir Genosar, Boulder, CO (US)

(73) Assignee: AKTIVAX, Inc., Broomfield, CO (US)

( * ) Notice: Subject to any disclaimer, the term of this patent is extended or adjusted under 35 U.S.C. 154(b) by 0 days.

(21) Appl. No.: 15/777,990

(22) PCT Filed: Nov. 23, 2016

(86) PCT No.: PCT/US2016/063660
§ 371 (c)(1),
(2) Date: May 22, 2018

(87) PCT Pub. No.: WO2017/151197
PCT Pub. Date: Sep. 8, 2017

(65) Prior Publication Data
US 2018/0346232 A1    Dec. 6, 2018

Related U.S. Application Data

(60) Provisional application No. 62/259,481, filed on Nov. 24, 2015, provisional application No. 62/381,503, filed on Aug. 30, 2016.

(51) Int. Cl.
*F16K 17/04* (2006.01)
*B65D 83/16* (2006.01)
(Continued)

(52) U.S. Cl.
CPC ............ *B65D 83/16* (2013.01); *A61M 5/2033* (2013.01); *A61M 5/2053* (2013.01); *B63C 9/19* (2013.01);
(Continued)

(58) Field of Classification Search
CPC ........ B65D 83/16; B65D 81/32; B65D 25/08; A61M 5/2033; A61M 5/2053; B63C 9/19; F41B 11/62
(Continued)

(56) References Cited

U.S. PATENT DOCUMENTS 2,206,818 A * 7/1940 Daniel ............... A62C 99/0027
                                                    137/68.3
2,375,314 A * 5/1945 Mills ....................... F41B 11/62
                                                    124/40

(Continued)

FOREIGN PATENT DOCUMENTS

DE    29914503 U1    12/1999
EP    3139976 B1 *   6/2019 .......... A61M 5/3202
(Continued)

OTHER PUBLICATIONS

International Search Report and Written Opinion for PCT Application No. PCT/US2016/063660, dated Aug. 18, 2017, 15 pages.
(Continued)

*Primary Examiner* — Minh Q Le
(74) *Attorney, Agent, or Firm* — Holzer Patel Drennan

(57) ABSTRACT

Several pressure cartridges and activation mechanism arrangements are disclosed which are configured to use less manual force to rupture the cartridge than current pressure cartridges and activation mechanisms. According to some embodiments, the activation mechanism requires lower manual activation force by using the pressure in the cartridge to do part of the rupturing work. The cartridge can be filled with compressed gas such as nitrogen and argon, or supercritical fluids such as carbon dioxide, and can be used to propel or operate several types of devices and mechanisms including medical drug auto-injectors, paintball guns, tire emergency inflation kits, and inflatable life vests.

11 Claims, 9 Drawing Sheets

(51) Int. Cl.
  *A61M 5/20* (2006.01)
  *F41B 11/62* (2013.01)
  *B63C 9/19* (2006.01)
  *B65D 25/08* (2006.01)
  *B65D 81/32* (2006.01)

(52) U.S. Cl.
  CPC ............. *B65D 25/08* (2013.01); *B65D 81/32* (2013.01); *F41B 11/62* (2013.01)

(58) Field of Classification Search
  USPC .................................. 137/68.29, 68.3, 68.11
  See application file for complete search history.

(56) References Cited

U.S. PATENT DOCUMENTS

| | | | | |
|---|---|---|---|---|
| 2,684,180 | A * | 7/1954 | Allen | F17C 13/04 222/5 |
| 3,010,520 | A * | 11/1961 | Seaberg | A62C 13/64 169/77 |
| 3,059,814 | A * | 10/1962 | Poncel | B63C 9/24 222/5 |
| 3,204,625 | A | 9/1965 | Shepherd | |
| 3,830,214 | A * | 8/1974 | Curtis | F41B 11/62 124/57 |
| 3,938,704 | A * | 2/1976 | Milgram | B67B 7/28 222/5 |
| 4,083,187 | A * | 4/1978 | Nagashima | F16K 17/403 137/68.3 |
| 4,666,062 | A * | 5/1987 | Pershall | B65D 83/60 137/68.3 |
| 4,790,824 | A * | 12/1988 | Morrow | A61M 5/30 604/143 |
| 5,361,524 | A * | 11/1994 | Karkau | F41B 11/62 124/41.1 |
| 6,254,447 | B1 | 7/2001 | Niemann | |
| 6,260,571 | B1 * | 7/2001 | Lind | B63C 9/24 137/580 |
| 6,689,093 | B2 * | 2/2004 | Landau | A61M 5/30 604/143 |
| 6,708,846 | B1 | 3/2004 | Fuchs et al. | |
| 6,783,509 | B1 * | 8/2004 | Landau | A61M 5/30 604/143 |
| 6,849,060 | B1 | 2/2005 | Brooks et al. | |
| 7,412,975 | B2 * | 8/2008 | Dillon, Jr. | F41B 11/62 102/440 |
| 8,206,360 | B2 * | 6/2012 | Edwards | G06F 19/3456 604/192 |
| 8,485,173 | B1 * | 7/2013 | Tseng | F41B 11/62 124/73 |
| 8,967,132 | B1 * | 3/2015 | Tseng | B63C 9/22 124/71 |
| 9,593,905 | B2 * | 3/2017 | Tseng | F41B 11/62 |
| 2002/0079285 | A1 | 6/2002 | Jansen et al. | |
| 2005/0236821 | A1 | 10/2005 | Hofmann et al. | |
| 2005/0267403 | A1 * | 12/2005 | Landau | A61M 5/30 604/70 |
| 2006/0054152 | A1 * | 3/2006 | Ambrico | A63H 5/04 124/71 |
| 2006/0180013 | A1 | 6/2006 | Reimers | |
| 2008/0086079 | A1 * | 4/2008 | Williamson | A61M 5/30 604/70 |
| 2011/0251546 | A1 * | 10/2011 | Sullivan | A61M 37/0015 604/22 |
| 2013/0192578 | A1 * | 8/2013 | Maeda | F41B 11/62 124/74 |
| 2014/0072678 | A1 * | 3/2014 | Jenkins | A47J 31/00 426/115 |
| 2014/0097106 | A1 * | 4/2014 | Broekaert | B65D 25/08 206/222 |
| 2015/0153004 | A1 * | 6/2015 | Stenzler | F17C 1/00 137/15.08 |
| 2015/0225048 | A1 * | 8/2015 | Lee | B63C 9/19 141/329 |
| 2015/0226517 | A1 | 8/2015 | Tseng | |
| 2016/0096600 | A1 * | 4/2016 | Zhang | B63C 9/19 441/93 |
| 2017/0029081 | A1 * | 2/2017 | Michalski | B63C 9/19 |
| 2017/0258583 | A1 * | 9/2017 | McCawley | A61F 2/1678 |
| 2017/0312433 | A1 * | 11/2017 | Edwards | A61M 5/2066 |

FOREIGN PATENT DOCUMENTS

| | | | |
|---|---|---|---|
| EP | 3492124 A1 * | 6/2019 | ......... A61M 5/2466 |
| WO | 2014037692 A1 | 3/2014 | |

OTHER PUBLICATIONS

Extended European Search Report for EP 16892924.8 dated May 31, 2019, 7 pages.

* cited by examiner

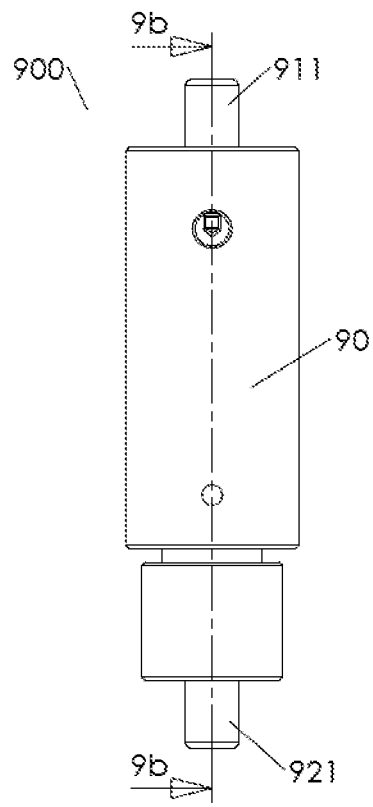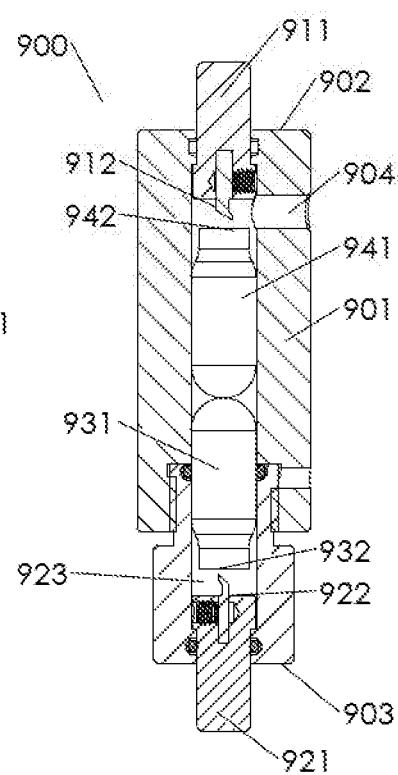
Figure 9a
Figure 9b
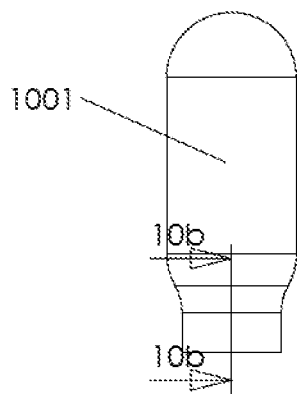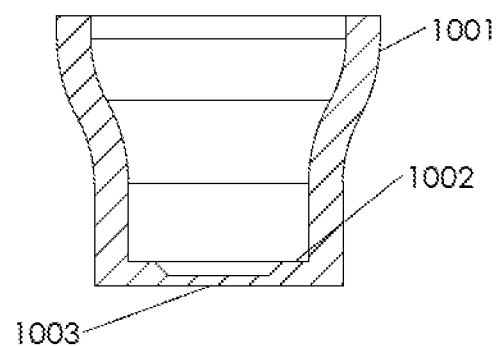
Figure 10a
Figure 10b

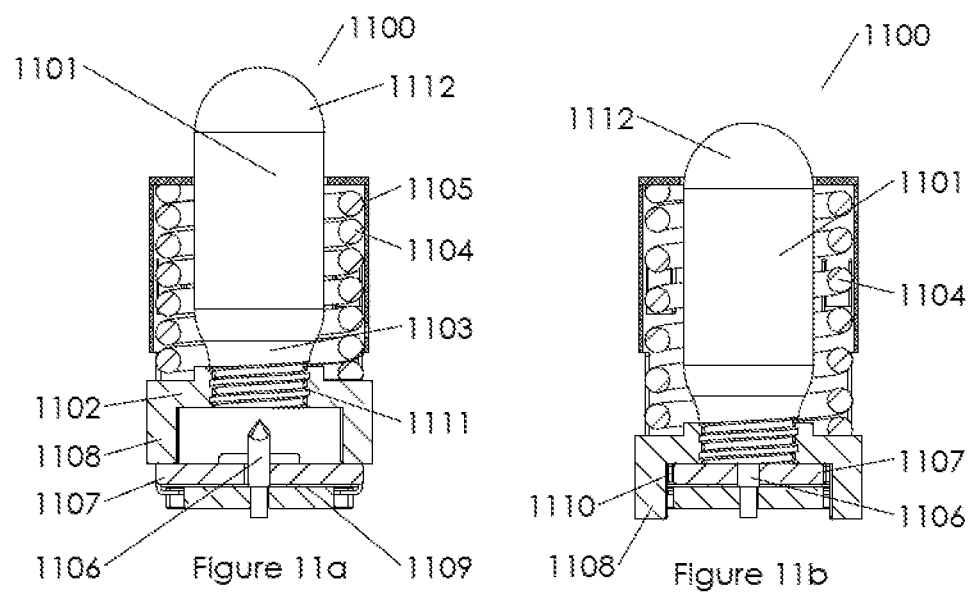

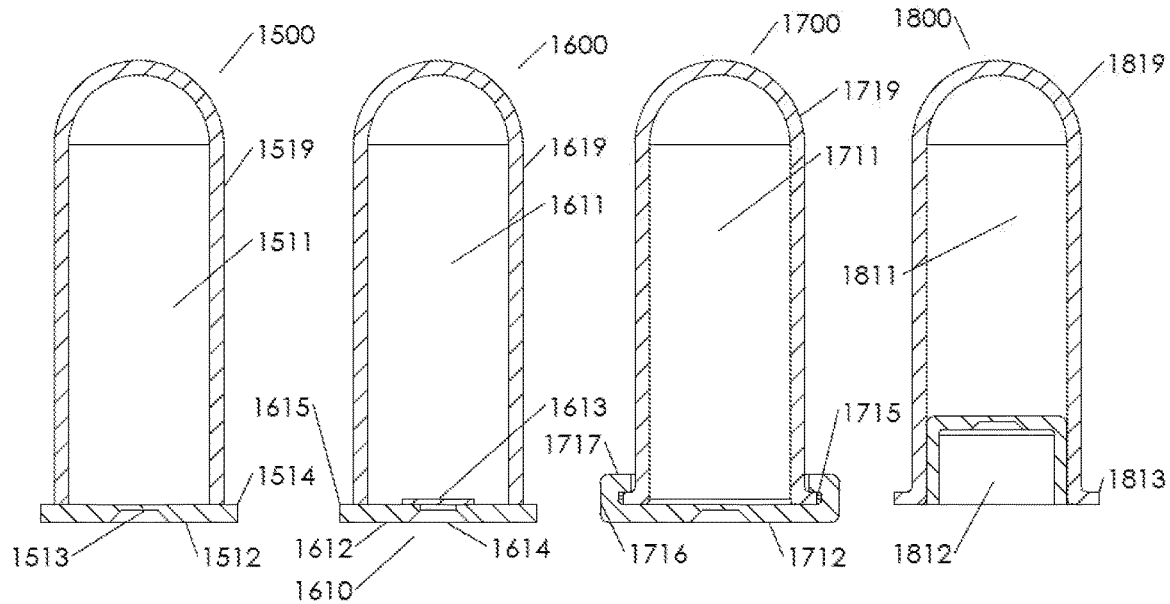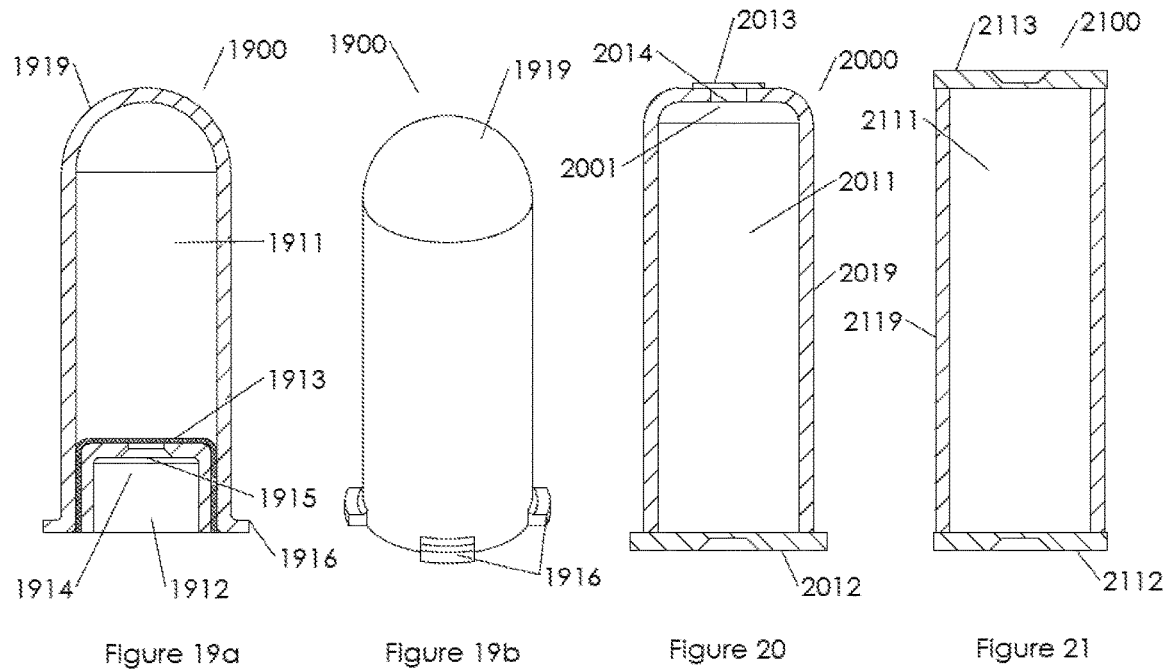

PRESSURE CARTRIDGE AND ACTIVATION MECHANISM

CROSS-REFERENCE TO RELATED APPLICATION(S)

This application is a 35 USC § 371 National Stage application of International Application No. PCT/US2016/063660, entitled "PRESSURE CARTRIDGE AND ACTIVATION MECHANISM," filed on Nov. 23, 2016, which claims priority to U.S. Provisional Patent Application No. 62/259,481, filed Nov. 24, 2015 and U.S. Provisional Patent Application No. 62/381,503, filed Aug. 30, 2016, all of which are hereby incorporated by reference in their entirety.

STATEMENT REGARDING FEDERALLY SPONSORED RESEARCH

This invention was made with government support under SBIR Phase II Contract No. W911QY-14-C-0048 awarded by the Department of Defense. The government has certain rights in the invention.

TECHNICAL FIELD

The present disclosure relates to rupturable pressurized cartridges. More specifically the present disclosure relates to pressure cartridges and mechanisms for rupturing the same.

BACKGROUND

Rupturable pressure cartridges are typically shaped as elongated tubular bodies, necked down at one end that is sealed with a thin metallic membrane, configured to be pierced by a sharp object. Pressurized cartridges, sometimes referred to as pressure canisters, can be filled by a variety of pressurized fluids such as compressed nitrogen or argon, or supercritical fluids such as carbon dioxide. The latter is common due to the high amount of energy that can be stored in a relatively small cartridge. Commercial cartridges come in a variety of loads, where some of the common loads are 1 gram, 8 grams and 12 grams.

Rupturable pressure cartridges have a broad variety of uses including medical drug auto-injectors, paintball guns, tire emergency inflation kits, and inflatable life vests. In practical applications the cartridge is associated with an activation mechanism that is configured to rupture the canister upon a user manipulation. To avoid accidental rupturing of the cartridge's membrane at a range of conditions, the membrane is made of a sufficiently thick metal. However, that means that more force needs to be applied to rupture the membrane.

Necking down the cartridge end allows the use of thinner membranes that are easier to rupture as that reduces the force applied by the pressurized fluid in the cartridge. However, in several applications it is desired to have a quick release of the pressurized fluid from the cartridge which requires a larger rupturable membrane. Between these different tradeoffs, carbon dioxide rupturable cartridges use membranes that are approximately 3 mm in diameter and require direct application of about 15-40 lb. by a sharp piercing object to the membrane to rupture. In several applications it is not practical or desired for the user to apply such high force to rupture the cartridge.

In many life vest designs a lever is implemented providing a force multiplier that significantly reduces the user activation force. In certain life vests designs and auto-injector designs, a preloaded spring and a spring release mechanism is used to activate the rupture of the cartridge. In certain activation mechanism this spring is preloaded to over 30 lb. The drawbacks of spring activation mechanisms include: (a) they are large and bulky, (b) a reinforced structure is required to hold the spring for elongated period of time, (c) they can be expensive, and (d) they bare the risk of premature activation.

It would therefore be desirable to have a rupturable pressurized cartridge that requires lower direct force to rupture the membrane.

SUMMARY

This summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

Various embodiments of the cartridge described herein are purposed to provide energy for operation of a consumer device. The cartridge and activation mechanism according to various embodiments described herein are configured to require lower manual activation force by performing a staged rupturing of the cartridge, comprising a first rupturing stage and a second rupturing stage where in the first rupturing stage a smaller rupture of the cartridge is performed, requiring less rupturing force, and at the second rupturing stage a larger rupture of the cartridge (as compared to the rupture in the first rupturing stage) is performed requiring higher rupturing force. The first rupturing stage allows discharge of just enough pressurized fluid from the cartridge that is applied toward automatically, pneumatically, perform the cartridge rupture of the second rupturing stage. The second rupturing stage allows higher discharge of the pressurized fluid from the cartridge to support the operation of the consumer device.

According to one aspect of the present disclosure the cartridge comprises a first membrane rupturable at the first rupturing stage, and a second membrane rupturable at the second rupturing stage. According to another aspect of the present disclosure the first membrane is configured to be ruptured at lower force than the second membrane. According to another aspect of the present disclosure the activation mechanism comprises a first rupturing member for rupturing the cartridge at the first rupturing stage, and a second rupturing member for rupturing the cartridge at a second rupturing stage. According to another aspect of the present disclosure the first rupturing member is configured to rupture the cartridge at a lower force and the second rupturing member is configured to rupture the cartridge at a higher force than the lower force.

The cartridge can have a first compartment of pressurized fluid sealed by a first rupturing member and a second compartment sealed by a second rupturable membrane.

In one arrangement of the present disclosure the arrangement comprises a first pressurized cartridge rupturable at the first rupturing stage and a second pressurized cartridge rupturable at the second rupturing stage.

According to another aspect of the present disclosure, a manufacturing process is taught providing a lower rupturing force to a member of a cartridge.

According to one aspect of the present disclosure the pressure cartridge comprises a flange. According to one aspect of the disclosure the flange is configured to support a spring. According to one aspect of the present disclosure the flange provides activation features.

According to one aspect of the present disclosure a rupturing member of a cartridge is configured to open a relatively large flow passageway in the cartridge's rupturable membrane at a relatively low force by cutting a cantilever in the membrane.

These and other aspects of the cartridge described herein will be apparent after consideration of the Detailed Description and the Figures herein. It is to be understood, however, that the scope of the claimed subject matter shall be determined by the claims as issued and not by whether given subject matter addresses any or all issues noted in the Background or includes any features or aspects recited in this Summary.

BRIEF DESCRIPTION OF THE DRAWINGS

Non-liming and non-exhaustive embodiments of the disclosed bearing isolator, including the preferred embodiment, are described with reference to the following figures, wherein like reference numerals refer to like parts throughout the various views unless otherwise specified.

FIGS. 9a and 9b illustrate an activation mechanism utilizing the pressure from the first cartridge to rupture a second cartridge according to various embodiments described herein;

FIGS. 10a and 10b illustrate a construction of a cartridge according to various embodiments described herein;

FIGS. 11a and 11b illustrate a pressure cartridge and activation mechanism arrangement where in the cartridge comprises a flange according to various embodiments described herein;

FIG. 15 illustrates a cartridge construction comprising a flange according to various embodiments described herein;

FIG. 16 illustrates a cartridge construction comprising a piercing membrane member according to various embodiments described herein;

FIG. 17 illustrates a cartridge construction with a crimp joint according to various embodiments described herein;

FIG. 18 illustrates a cartridge construction with co-annular cartridge body and lid according to various embodiments described herein;

FIGS. 19a and 19b illustrate a cartridge construction where the membrane member extends between the cartridge body and the lid according to various embodiments described herein;

FIG. 20 illustrates a cartridge construction where the cartridge body comprises a piercing region according to various embodiments described herein;

FIG. 21 illustrates a cartridge construction where the cartridge is formed with two lids according to various embodiments described herein;

DETAILED DESCRIPTION

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following description is, therefore not to be taken in a limiting sense.

Figure 1A:
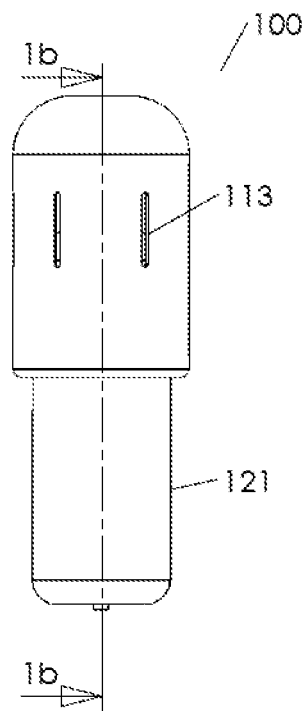
FIGS. 1a to 1d illustrate a pressure cartridge and activation mechanism arrangement, comprising a cartridge with two rupturable membranes, and a sealed actuation chamber is sealed by an O-ring, according to various embodiments described herein.
Figure 1B:
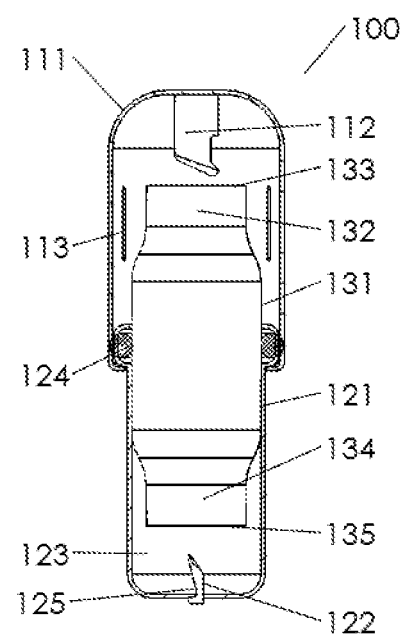

FIG. 1a to FIG. 1b illustrate a pressure cartridge and activation mechanism arrangement 100, configured to rupture the cartridge to rapidly release the pressurized fluid from the cartridge 131 while keeping the activation force low. The pressure cartridge and activation mechanism arrangement 100 is purposed to supply pressure or energy to a consumer device such as a life vest or a medical drug delivery auto-injector.

The cartridge 131 can be made from a rigid, elongated tubular wall comprising a first end 134 sealed by a first rupturable membrane (hereafter sometimes referred to as first membrane), and a second end 132 sealed by a second rupturable membrane (here after sometimes referred to as a second membrane). The cartridge 131 is moveably disposed in a first casing 121 comprising a first rupturing member 122 confronting the first membrane 135. An O-ring seal 124 provides a fluid tight seal between the cartridge 131 and the first casing 121. A pressure chamber 123 is formed between the cartridge 131 and the first casing 121. A second casing 111 is moveably disposed over the first casing 121 and the cartridge's second end 132, and comprising a second rupturing member 112, in a confronting position to the second membrane 133.

FIG. 1b illustrates a longitudinal cross section of the arrangement 100 at a pre-use configuration. The first rupturing member 122 and the second rupturing member 112 are configured such that lower force is required for the first rupturing member 122 to rupture the first membrane 135 (hereafter sometimes referred to as the first rupture) than the force required for the second rupturing member 112 to rupture the second membrane 133 (hereafter sometimes referred to as the second rupture). This can be achieved by at least one of the sharpness, roundness, diameter, cut geometry, hardness, and other characteristics of each rupturing member 112/122. In one arrangement the force required for the first rupture is lower than 8 lbf, and the force required for the second rupture is greater than 20 lbf.

In some arrangements the control of the first and second rupturing forces can be supplemented by design of the rupturable membranes materials, thickness, and manufacturing process. In one arrangement the second membrane 133 is electroplated with zinc and the first membrane 135 is either coated with a thinner layer of zinc or is not coated at all, attributing to a lower rupturing force of the first membrane 135. Lab experiments have demonstrated that the difference in rupturing force of one type of rupturing member and one type of membrane when it was electroplated and not electroplated was 20-22 lbf vs. 6-8 lbf respectively.

The second rupturing opens a significantly larger opening in the second membrane 133 to allow instant supply of energy to the consumer device that the arrangement 100 is serving. The force required for the second rupturing may not be practical for direct application by a user or a device. The first rupturing force is tuned to be practical for direct activation by a user or a device.

The shank of the first rupturing member 122 may comprise a curved out section 125 configured to facilitate venting of the pressurized fluid from the cartridge 131. During the first rupture, the tip of the first rupturing member 122 causes plastic deformation of the first membrane 135, which gives for a substantial flow path for the pressurized fluid when the carved out section 125 presented at the cut area of the first membrane 135. The cartridge 131 is filled with pressurized fluid in a gas state or in a dual-phase super critical state. Examples of pressurized fluids that can be filled in the cartridge 131 include carbon dioxide, nitrogen and argon.

Figure 1C:
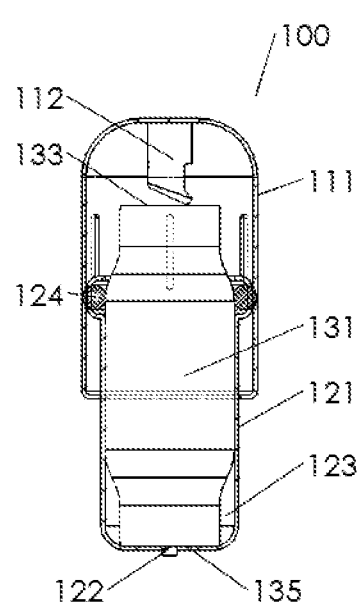

FIG. 1c illustrates the arrangement 100 at the first rupture state. The first casing 121 and the second casing 111 are moved toward each other such that the second rupturing member 112 pushes against the second membrane 133 and moves the cartridge 131 relative to the first casing 121 causing the first rupturable member 122 to pierce the first membrane 135 (the first rupture). The first rupture pressurizes the pressure chamber 123, biasing the cartridge 131 toward the second rupturing member 112. Even a relatively slow release of the pressurized fluid from the first rupture rapidly pressurizes the pressure chamber 123.

In one arrangement the pressurized fluid is carbon dioxide at a super critical state, the cartridge 131 diameter is ⅜" and at room temperature the biasing force toward the second rupturing member 112 can be greater than 500 Newton, or 100 lbf, sufficient force for the second rupturing.

Figure 1D:
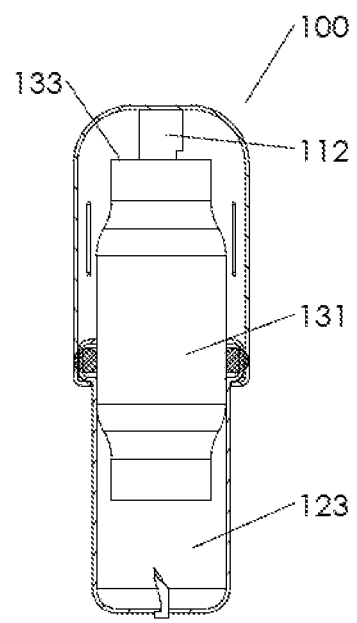

The O-ring seal 124 prevents the fluid from escaping the pressure chamber 123 providing that the maximum pressure is applied to forcing the cartridge 131 toward the second rupturing member 112. FIG. 1d illustrates the arrangement 100 at the second rupturing state. The pressure in the pressure chamber 123 moved the cartridge 131 toward the second membrane 133 and caused the second rupturing member 112 to rupture the second membrane 133 (the second rupture). The second rupture is sufficiently large to rapidly release the pressurized fluid from the cartridge 131, through vent holes 113 toward the consumer device.

The process illustrated in FIGS. 1a to 1d demonstrates an arrangement 100 for rapidly releasing a pressurized fluid from a cartridge 131 that requires low activation force by a user, by using the pressurized fluid in the cartridge 131 for self-rupturing. This arrangement 100 eliminates the need for mechanical levers, high-force springs, and complex, expensive and bulky constructions that are implemented in the prior art.

Figure 2:
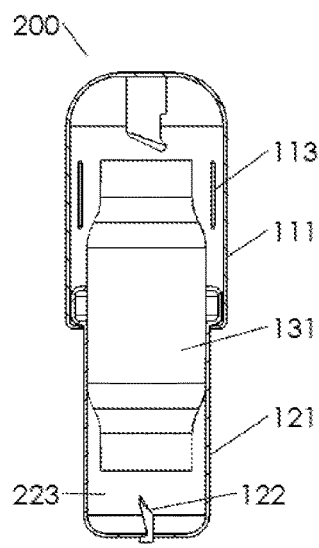
FIG. 2 illustrates a pressure cartridge and activation mechanism arrangement wherein the activation chamber is not sealed by an O-ring according to various embodiments described herein.

FIG. 2 illustrates another embodiment of a pressurizing arrangement 200, similar to the arrangement 100 of FIG. 1a-d but where the pressure chamber 223 is not sealed between the cartridge 131 and the first casing 121. At the first rupture the pressurized fluid can escape between the first casing 121 and the cartridge 131. However, sufficient pressure develops in the pressure chamber 223 immediately after the first rupture to force the second rupture, and thereafter the remaining pressurized fluid vents out through openings 113. By avoiding the seal between the cartridge 131 and the first casing 121, a friction component is eliminated making the first rupture easier. In addition, by allowing the pressure chamber 223 to vent before the first rupture, the air or other gas that is present in the pressure chamber 223 before the first rupture doesn't compress as the cartridge 131 moves toward the first rupturing member 122 further reducing the force required for activation of the first rupture.

In one arrangement the first rupture is activated by acceleration force rather than a movement of one of the casing portions 121 an 111. Such an acceleration can be caused in many ways including by a drop shock and shaking the device.

Figure 3:
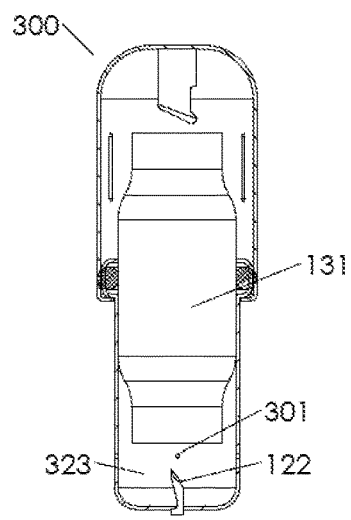
FIG. 3 illustrates a pressure cartridge and activation mechanism arrangement wherein the activation chamber comprises a pressure bleeding passageway according to various embodiments described herein.

FIG. 3 illustrates another embodiment of a pressurizing arrangement 300, similar to the arrangement 100 of FIG. 1a-d but where the pressure chamber 323 includes one or more bleeding holes 301. The bleeding holes 301 prevent pressure from building in the pressure chamber 323 during activation of the first rupture when the cartridge 131 moves toward the first rupturing member 122, and resisting the activation. The bleeding holes 301 are sufficiently small as to not substantially affect the pressure in the pressure chamber 323 after the first rupture that is required for the pneumatic activation of the second rupture.

Figure 4:
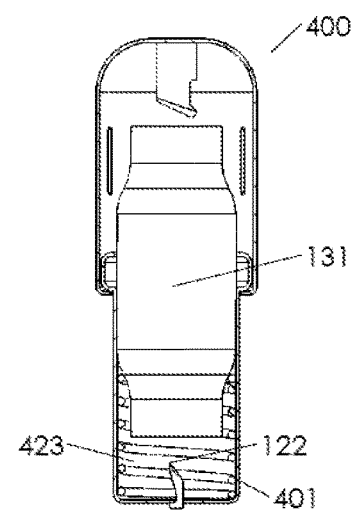
FIG. 4 illustrates a pressure cartridge and activation mechanism arrangement where in the cartridge is biased away from the first rupturing member by a spring according to various embodiments described herein.

FIG. 4 illustrates another embodiment of a pressurizing arrangement 400 substantially similar to the arrangement 200 of FIG. 2 but where a spring 401 is disposed in the pressure chamber 423 to bias the cartridge 131 away from the first rupturing member 122 to prevent premature or accidental activation of the arrangement 400.

Figure 5:
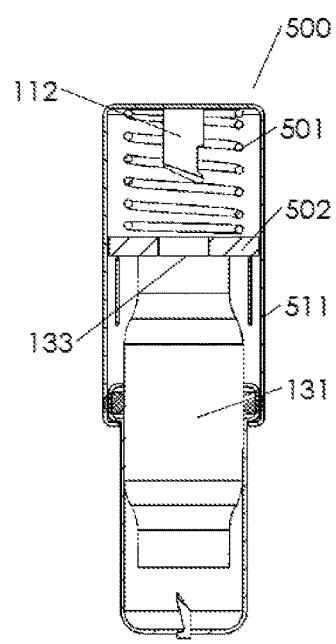
FIG. 5 illustrates a pressure cartridge and activation mechanism arrangement wherein a spring controls a threshold activation force of the second cartridge rupture according to various embodiments described herein.

FIG. 5 illustrates another embodiment of a pressurizing arrangement 500, similar to the arrangement 100 of FIG. 1a-d but where a spring 501 is axially disposed between the cartridge 131 and the second casing 511, and defines a minimum threshold external axial force for the second rupturing element 112 to reach the second membrane 133, to start the second rupture. A washer 502 interfaces between the spring 501 and the cartridge 131, and during the second rupture the second rupture member 112 accesses the cartridge 131 through the opening in the washer 502.

Figure 6:
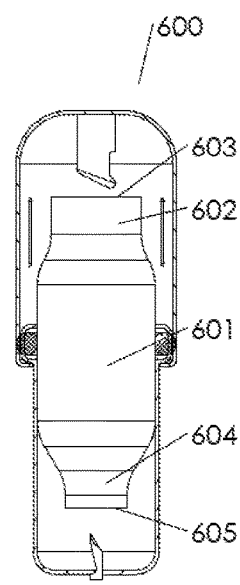
FIG. 6 illustrates a pressure cartridge and activation mechanism arrangement wherein the cartridge comprises a first necked end accommodating a first rupturable membrane having a smaller diameter than the second necked end accommodating the second rupturable membrane according to various embodiments described herein.

FIG. 6 illustrates another embodiment of a pressurizing arrangement 600, similar to the arrangement 100 of FIG. 1a-d but wherein the cartridge 601 comprises a narrower neck on its first end 604 than on its second end 602. Because of the smaller diameter of the first end 604 the pressurized fluid in the cartridge 601 exerts lower force on the first rupturable membrane 605, allowing safe and reliable implementation of thinner membrane or membrane made of lower strength materials, which require less force to rupture relative to the second rupture.

Figure 7:
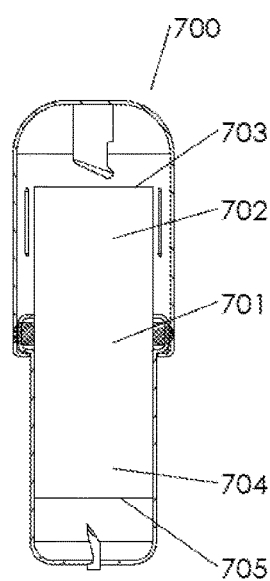
FIG. 7 illustrates a pressure cartridge and activation mechanism arrangement wherein the cartridge has a tubular form and no necked regions at the membrane ends according to various embodiments described herein.

FIG. 7 illustrates another embodiment of a pressurizing arrangement 700, similar to the arrangement 100 of FIG. 1a-d but wherein the cartridge 701 has a tubular shape which doesn't neck down at the ends. This shape features a manufacturing simplicity as the cartridge can be made from a portion of a tube rather than through compression and calendaring process. The first rupturable membrane 705 is joined to the first end 704 and the second rupturable membrane 703 is joined to the second end 702, by one of the processes known in the art such as welding, arch welding, and point welding.

One skilled in the art would readily understand that any combination of the features of the arrangements of FIGS. 1-7 is possible and that they are presented separately in this disclosure for the purpose of simplicity of the teaching.

Figure 8A:
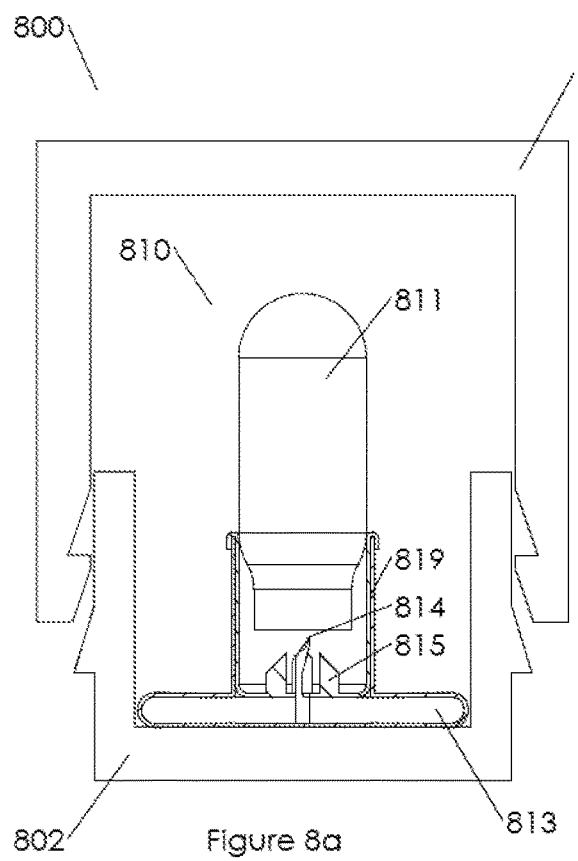
FIGS. 8a to 8c illustrate a pressure cartridge and activation mechanism arrangement wherein the cartridge has one rupturable membrane and the activation mechanism comprises a bellows actuator according to various embodiments described herein.
Figure 8B:
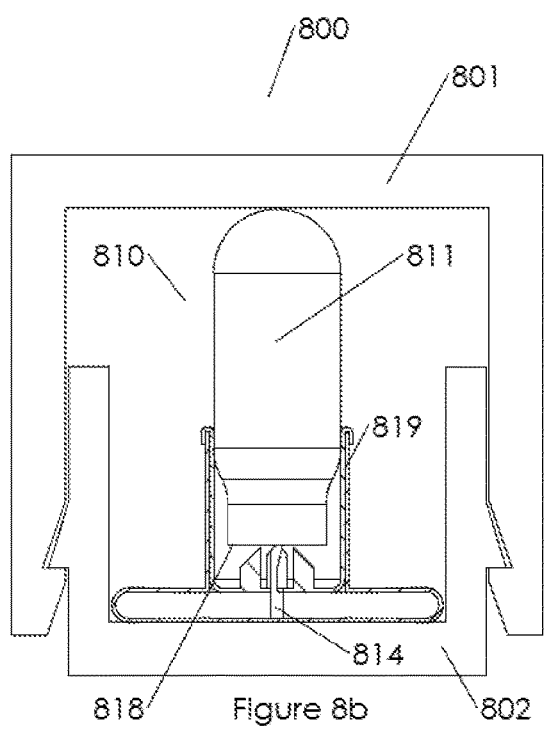
Figure 8C:
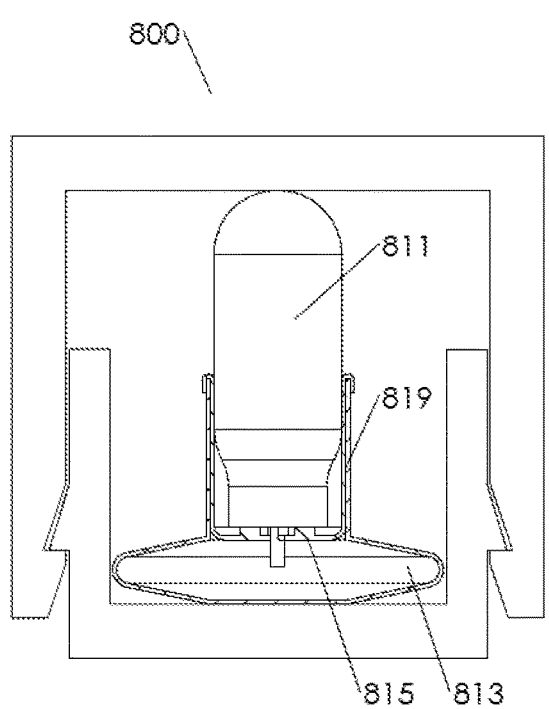

FIGS. 8a to 8c illustrate another embodiment of a pressurizing arrangement 800. FIG. 8a illustrates the pre-use state. The cartridge 811 is axially moveably disposed in a tubular neck 819 of a bellows 813. A first rupturing element 814 and second rupturing elements 815 are also disposed in the tubular neck 819 the bellows 813 such that when the bellows 813 expand the neck 819 and rupturing elements 814, 815 move with it toward the cartridge 811. The cartridge and bellows assembly 810 (including cartridge 811 and bellows 813) is enclosed in a frame that includes a base portion 802 and a top portion 801.

FIG. 8b illustrates the cartridge 811 at the first rupture state. The top portion of the frame 801 is moved toward the base portion 802 until the two interlock. Along this process the cartridge 811 is moved downward and the first rupturing element 814 ruptures the membrane 818 (the first rupture), allowing the pressurized fluid to fill the bellows 813.

FIG. 8c illustrates the second rupture state of arrangement 800. The pressurized fluid expands the bellows 813, moving the tubular neck 819 relative to the cartridge 811, and causes the second rupturing element 815 to create a larger rupture in the membrane 818 (the second rupture) allowing rapid release of the pressurized fluid from the cartridge 811. The pressurized fluid escapes from the bellows 813 from a gap in between the neck 819 and the cartridge 811.

In one arrangement, the cartridge and bellows arrangement 810 comprises a pressure release valve or a rupturable section that opens when the pressure in the bellows 813 exceeds a certain threshold, allowing faster release of the pressurized fluid from the bellows 813. The bellows 813 can be made from a variety of materials including metals such as stainless steel or plastic.

In one arrangement the first rupture member 814 sits on top of the second rupturing membrane 815. In other words the two rupturing members 814/815 are the same body where the part closer to the cartridge 811 is configured for a lower force rupture that releases the pressurized fluid at a lower rate, and the base part of that member is configured to rupture the cartridge at a higher force and create a larger opening in the cartridge 811 to release the pressurized fluid at a higher rate.

FIGS. 9a and 9b illustrate another embodiment of a pressurizing arrangement 900 in a pre-use state. A first cartridge 931 and a second cartridge 941 are axially disposed in a tubular housing such that their rupturable membranes 932 and 942 respectively are facing opposite directions. A first actuator 921 is disposed at the first end 903 of the housing 901 and it holds a first rupturing member 922 in a confronting position to the first rupturable membrane 932. A second actuator 911 is disposed at the second end 902 of the housing 901 and it holds a second rupturing member 912 in a confronting position to the second rupturable membrane 942. The rupturing force of the first rupturing membrane 932 by the first rupturing member 922 (the first rupture) is lower than the rupturing force of the second rupturing membrane 942 by the second rupturing member 912 (the second rupture). At the first rupturing state, at least one of the actuators 911 and 921 are moved inward toward the housing 901 such that the second rupturing member 912 pushes the second cartridge 941, which pushes the first cartridge 931 against the first rupturing member 922 to cause the first rupture. The pressurized fluid fills the pressure chamber 923 and exerts force on the first cartridge 931 to push the second cartridge 941 toward the second rupturing member 912 to cause the second rupture. The pressurized fluid is released toward the consumer device through hole 904. Hole 904 can be tapped or otherwise configured to receive a connector, a fitting, a tube, a hose, or other instruments for transporting the pressurized fluid to a consumer device. In one arrangement cartridges 931 and 941 are merely two compartments of one cartridge.

FIGS. 10a and 10b illustrate a construction of a pressure cartridge 1001 comprising a rupturable membrane 1003. A co-annular rigid section 1002 provides for a smaller diameter membrane 1003 and hence a thinner or softer membrane can be used to safely and reliably withstand the pressure of the pressurized fluid in the cartridge 1001, and at the same time require lower rupturing force. This construction can be applied to any of the cartridges of the present disclosure.

FIGS. 11a and 11b illustrate another embodiment of a pressurizing arrangement 1100. FIG. 11a illustrates the arrangement 1100 in a pre-use state. The pressure cartridge 1101 comprises a body 1112 and a flange 1102 at its first end 1103, secured to the body 1112 via a thread 1111. In other arrangements, the flange 1102 is formed as an integral part of the body 1112 by one of the processes known in the art including machining, compression forming, punching and rolling. In other arrangements the flange is joined to the body 1112 by one of the processes known in the art including at least one of a fastener, a screws, welding, soldering, adhering, press fitting, crimping, or a combination of the formers. A spring 1104 is supported by a casing 1105, biases the flange 1102 toward the rupturing member 1106 which is supported by a base plate 1109. The flange 1102 comprises two downward facing legs 1108 that lean against a rotating plate 1107 and prevent the cartridge 1101 from moving toward the rupturing member 1106. The rotating plate 1107 acts as an activation mechanism, and the flange 1102 restrains the cartridge 1101 from moving in the axial direction by interfacing with the activation mechanism 1107.

FIG. 11b illustrate the ruptured state where the rotating plate 1107 is turned such that openings 1110 in the rotating plate 1107 line up with the flange legs 1108 allowing it to drop down and cause the rupturing member 1106 to pierce the cartridge 1101. The flange 1102 can be of a variety of forms know in the art including a ledge, a flat rim, collar, a rib or have a round perimeter or a perimeter to provide at least one of a support to a spring and a ledge for holding the cartridge from moving. In this state the flange 1102 doesn't interface with the activation mechanism 1107, allowing the cartridge 1101 to move in an axial direction.

Figure 12A:
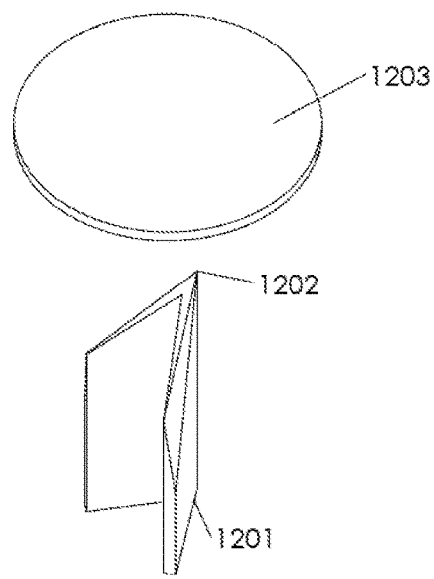
FIGS. 12a to 12c illustrate a rupturing member and a rupturing process according to various embodiments described herein.
Figure 12B:
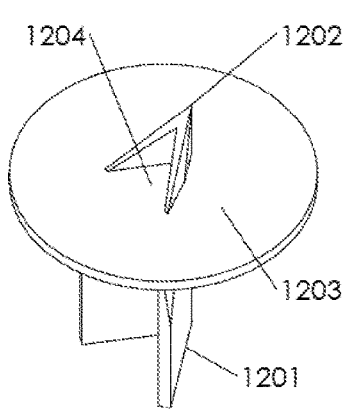
Figure 12C:
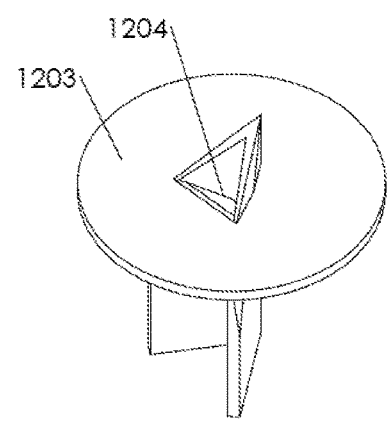

FIGS. 12a to 12c illustrate one design of a rupturing member 1201 and a process of rupturing membrane 1203. Rupturing member 1201 is configured to open a relatively large passageway for the pressurized fluid to vent from a cartridge, at a relatively low rupturing force. FIG. 12a illustrates the pre-rupture state. Rupturing element 1201 has a V shape profile with a sharpened tip 1202 at its rupturing end. FIG. 12b illustrates an intermediate rupturing step where in the rupturing member 1201 makes a V-shape cut in the membrane 1203, essentially forming a V-shaped cantilever 1204. FIG. 12c illustrates the ruptured state of the membrane 1203, wherein the pressure in the cartridge bends out the cantilever 1204, opening a substantial flow passageway in the membrane 1203. The V shaped rupture member 1201 produces a relatively large opening in the membrane 1203 by making a relatively small cut, and hardly any plastic deformation in the membrane 1203 which requires less force to perform compared for instance to a needle which causes substantial deformation in the membrane during rupture but produces little gap between the needle and the opening in the membrane.

Figure 13:
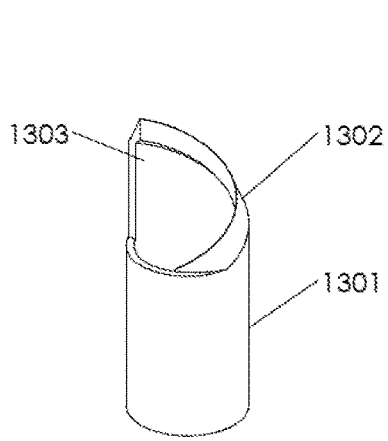
FIG. 13 illustrate another rupturing member according to various embodiments described herein.

FIG. 13 illustrate another rupturing member 1301 that can open a relatively large flow passageway in a membrane at a relatively low rupturing force. Like in FIG. 12, rupturing member 1301 is configured to cut a cantilever in the membrane that will be deformed by the pressure in the cartridge to open a substantial flow passageway in return to a relatively small cut in the membrane and with very little deformation of the membrane by the rupturing member 1301. The rupturing tip 1302 of the rupturing membrane 1301 has the form of a helical blade configured to make a circular cut in a membrane. The circular cut can be of about 180 degrees and act like a cantilever that can be deformed by the pressure to open a substantial passageway in the membrane. The inner diameter at the root of the cutting blade 1303 is larger than the inner diameter of the blade 1302 to allow the cantilever of the membrane to more freely bend toward the shank of the rupturing membrane 1301.

Figure 14A:
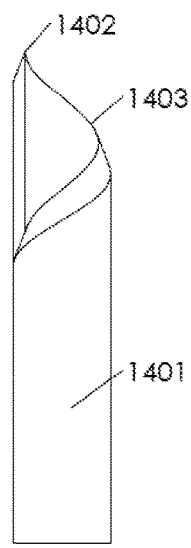
FIGS. 14a and 14b illustrate another rupturing member according to various embodiments described herein.
Figure 14B:
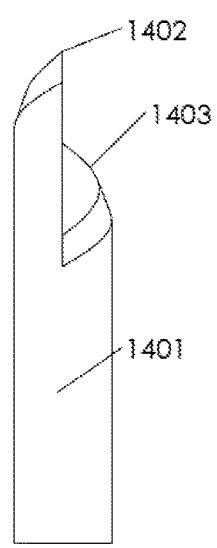

FIG. 14 illustrates another rupturing member 1401 that can open a relatively large flow passageway in a membrane at a relatively low rupturing force. Rupturing member 1401 comprises a sharp tip 1402 leading to a spiral blade 1403, such that during rupturing the membrane is cut at a single point, and the rupturing member 1401 produces minimal deformation of the membrane. The crescent shape cut that the rupturing member 1401 cuts in the membrane forms a cantilever that yields to the pressure in the cartridge and opens a significant venting passageway in the membrane.

FIG. 15 illustrates an embodiment of a pressure cartridge arrangement 1500 comprising a body 1511, comprising a receptacle 1519 and a lid 1512, joined in a fluid tight fashion to form a pressure chamber. In one arrangement the cartridge arrangement 1500 is filled with compressed gas such as carbon dioxide, nitrogen or argon. The lid 1512 may be joined to the receptacle 1519 by one of the means known in the art including welding, point welding, induction welding, laser welding and friction welding. The lid 1512 comprises a thinned down section 1513, providing a piercing region for piercing the cartridge 1500 with a piercing member. In one configuration the piercing region 1513 comprises force concentrators to facilitate the rupture by the piercing member. The diameter of the lid 1512 is larger than the diameter of the receptacle 1511 thereby forming a flange 1514 for interfacing the cartridge 1500 with an activation mechanism (or piercing mechanism), such as a spring.

FIG. 16 illustrates an embodiment of a cartridge arrangement 1600 similar to the cartridge arrangement 1500 of FIG. 15, but where the piercing region 1610 comprises an opening in the body 1611, and a membrane 1613 that seals over the opening 1614 in a fluid tight fashion. The membrane 1613 is configured to facilitate the rupture by a rupturing pin, compared to the other wall sections of the body 1511, by featuring at least one of a thinner wall, a softer material property (easier for penetration by a piercing pin), force concentrator, and a more brittle material property (easier to shutter by the piercing pin). The membrane 1613 may be joined to the lid 1612 by one of the means known in the art including welding, point welding, laser welding induction welding, friction welding, gluing, soldering and adhesion. The advantage of implementing a membrane as opposed to a thinned-down area in the lid is better control on the membrane thickness and mechanical properties. The circumference of the lid 1612 extend beyond the diameter of the body 1611 to form a flange 1615. The flange 1615 is integral to the lid 1612. The flange 1615 may be a continuous circular protrusion beyond the diameter of the body 1611, or one or more local radial protrusions in various forms. The body 1611 may be made of various materials including steel, stainless steel, aluminum, a metal alloy and plastics.

FIG. 17 illustrates an embodiment of a cartridge arrangement 1700 similar to the cartridge arrangement 1500 of FIG. 15, but where the body 1711 comprises a lid 1712 joined to the receptacle 1719 by a crimp 1716. The receptacle 1711 comprises a flange 1715, and the lid 1712 is formed around the flange 1715 to form a fluid tight crimp joint 1716. The crimp joint 1716 may be advantageous to avoid the welding step in the manufacturing process. In one configuration sealing is enhanced by at least one of adding a sealant, an adhesive, a gasket and an O-ring to the crimp joint. The crimp joint 1716 forms a flange 1717 that extends beyond the diameter of the body 1711, and the receptacle 1719.

FIG. 18 illustrates an embodiment of a cartridge arrangement 1800 similar to the cartridge arrangement 1500 of FIG. 15, but where the body 1811 comprises a lid 1812 comprising a formed cylindrical wall that is located co-annularly with the receptacle 1819. This arrangement facilitates centering of the lid 1812 with the receptacle 1819 during the manufacturing process. The lid 1812 may be joined to the receptacle 1819 by a press fit. A sealant or an adhesive may be added in the joint between the receptacle 1819 and the lid 1812. The edges of the receptacle 1819 are flared outward to form a flange 1813. The flange 1813 is integral of the body 1811

FIG. 19a illustrates an embodiment of a cartridge arrangement 1900 similar to the cartridge arrangement 1800 of FIG. 18, but where the piercing region 1914 comprises a membrane 1913 that seals over opening 1915. The membrane 1913 co-annularly extends between the body 1911 and the lid 1912, eliminating the need to seal the membrane 1913 to the lid 1912 around the hole in the lid 1912. In one configuration at least one of the membrane 1913 and the lid 1912 extends to form a crimp around the flange of the body 1911. The body 1911 comprises a receptacle 1919 and a lid 1912 where in the flange 1916 is integral with the receptacle 1919. FIG. 19b illustrates the cartridge 1900 in an angled view showing an array of ledges 1916 extending from the cylindrical body 1919, that form the flange.

FIG. 20 illustrates an embodiment of a cartridge arrangement 2000 similar to the cartridge arrangement 1500 of FIG. 15, but where the body 2011 comprises a receptacle 2019 comprising a piercing region 2001, comprising an opening in the body 2014. A membrane 2013 seals over the opening 2014 in the body 2011 similarly to the piercing region 1610 arrangement of FIG. 16. In one configuration the membrane 2013 is a thinned down, integral section in the body 2011, rather than a joined member, similarly to the piercing region 1610 of FIG. 16. In one arrangement the lid 2012 doesn't have a piercing region.

FIG. 21 illustrates a cartridge arrangement 2100 comprises a body 2111, comprising a cylindrical receptacle 2119 sealed on both ends with lids 2112 and 2113. In one arrangement only one of the lids 2112 and 2113 comprises a piercing region.

Figure 22A:
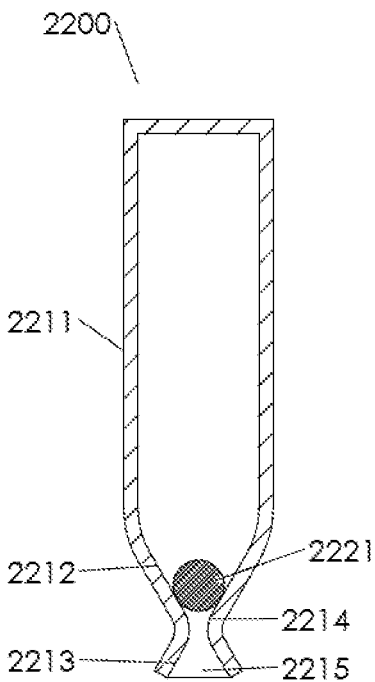
FIGS. 22a-22c illustrate a cartridge arrangement construction where the cartridge is sealed with a low melting point material according to various embodiments described herein.
Figure 22:
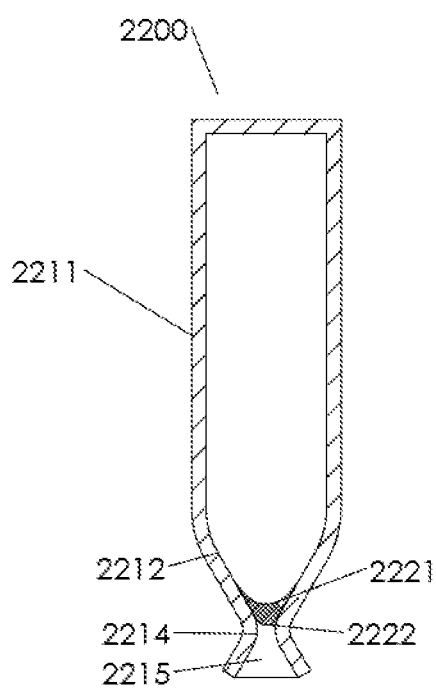

FIG. 22a illustrates a cartridge 2200 for containing a pressurized substance, comprising a body 2211 of a cylindrical form. The first end of the body 2211 comprises a conical funnel 2212 tapering toward a neck 2214, that leads to an opening 2215. The body 2211 is made from a relatively high melting point material such as steel, stainless steel, aluminum, or a polymer. A sealing member 2221 in a form of a bid, made from a low melting temperature material is disposed at the conical section 2212. The sealing member can be made from a polymer or a metal alloy. The sealing member 2221 is moveable relative to the funnel 2212, allowing filling the cartridge 2220 with the pressurized substance. FIG. 22b illustrates the cartridge 2200 after it has been filled and sealed. The sealing member 2221 was heated up to a temperature above its transition temperature, causing the edges of the sealing member to deform and conform to the conical end 2212 shape and form a fluid tight seal over the opening 2215 of the cartridge 2200. The central area of the sealing member 2221 forms a membrane 2222 across the neck 2214 of the cartridge 2200. Depending on the choice of material for the cartridge 2200 and the sealing member 2221 this seal may comprise a weld, a solder, or adhesion. The material of the sealing member 2221 is a soft material that is relatively easy to penetrate with a piercing member. An example of a sealing member 2221 material is solder which has both a low melting point and is relatively soft. The cartridge body 2211 further comprises reverse conical end 2213 which facilitate directing the piercing member toward the member 2221. In one arrangement the sealing member 2221 is pre-made to a shape different than a sphere, for instance to a shape more resembling the sealed shape shown in FIG. 22b.

In some embodiments, the sealing member 2221 is made of a composition of a low melting point substance and a higher melting point substance such that: (a) the center area is preformed to the desired rupturable membrane shape and is made from the higher melting point material, and (b) the circumference is made from a lower melting point material and is formed to facilitate the sealing process between the sealing member 2221 and the body 2211. In one arrangement the low melting point material is a polymer. In another arrangement the low melting point material is a metal alloy.

In one arrangement the sealing process comprises heating the neck area of the cartridge 2200 to cause the low melt point material to melt and form a sealed joint between the neck 2214 of the cartridge 2200 and the sealing member 2221. In one arrangement, the sealing process comprises spinning the cartridge to control the shape in which the molten sealing member 2221 will set in, i.e. by applying centripetal force to the molten sealing member 2221. This heating process of the sealing member 2221 may comprise applying radiation, conduction, heating with a laser beam, and magnetic induction.

In one arrangement the cartridge is made from a poor electric conducting material such as stainless steel and the sealing member comprises a good conductor with good magnetic properties. In this arrangement the sealing step comprises applying magnetic induction (Eddie current) that would cause the sealing member to heat up causing local temperature rise at the sealing area without heating the entire cartridge 2200. The magnetic induction can be achieved by at least one of spinning a magnetic field around the cartridge and spinning the cartridge in a magnetic field.

Figure 22C:
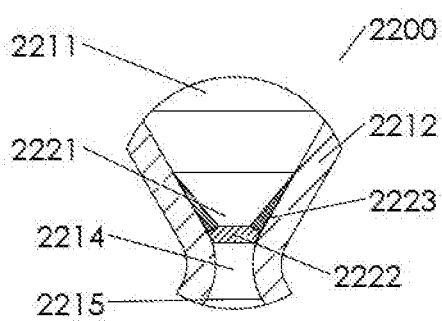

FIG. 22c illustrates another arrangement of the sealing member 2221 where it is made of a composition of membrane section 2222 made from a first material, and sealing section 2223 made from a second material. The first material has a higher melting point than the second material. The sealing process comprises heating the sealing member 2221 to a temperature above the melting point of the second material and lower than the melting point of the first material, causing the sealing section 2223 to seal against the cartridge 2211 while the membrane section 2222 retains its original shape.

Figure 23A:
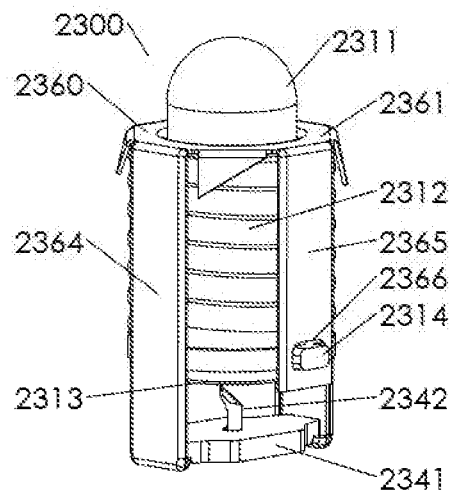
FIGS. 23a-23c illustrate a cartridge and activation mechanism arrangement wherein the cartridge comprises a flange, and the activation mechanism is released by a radial motion according to various embodiments described herein.
Figure 23B:
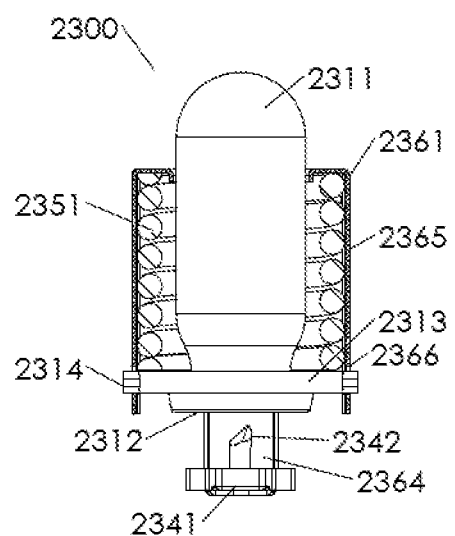
Figure 23C:
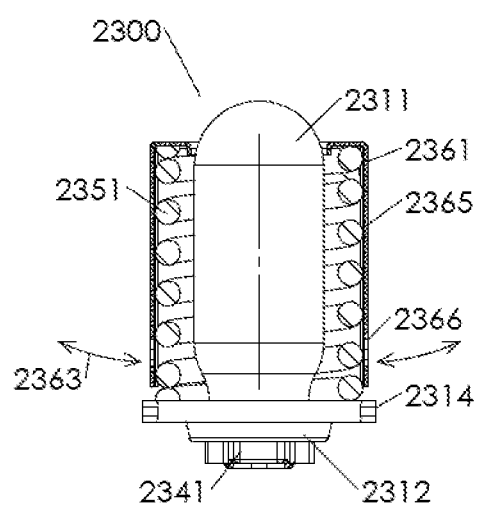

FIGS. 23a and 23b illustrate another arrangement of a pressurized cartridge activation mechanism 2300, similar to the arrangement of FIG. 11, in a pre-activation state. The activation mechanism 2300 comprises a body 2360, comprising a flange 2361 with a central opening in which the pressurized cartridge 2311 is disposed and can move freely. A pair of support arms 2364 extend from the flange 2361, in an axial direction and support a piercing plate 2341. A piercing member 2342 is positioned at the center of the piercing plate 2341, confronting the openable region 2312 of the cartridge 2311. The body 2360 further comprises two activation arms 2365. The cartridge 2311 comprises a flange 2313. Detent teeth 2314 extend radially from the flange and interface with opening 2366 in the activation arms 2365, preventing the cartridge 2311 from axially moving. The cartridge flange 2313 is biased by spring 2351 toward the piercing member 2342. FIG. 23c illustrate the activation mechanism 2300 at the activated state. The activation arms 2365 moved outwards in the direction shown by arrows 2363, releasing the detent teeth 2314 and allowing the downward movement of the cartridge 2311, and causing the piercing member (not shown) to penetrate the openable region 2312 and open the cartridge 2311, allowing the pressurized substance to exit the cartridge 2311.

One skilled in the art would understand that all of the arrangements described in the Figures can be manually activated or activated by a device. An example of activation by a device is a loaded compression spring, held in a mechanism that releases it when it gets wet or when the environment pressure exceeds a threshold value as in automatic inflators of life vests. Importantly, the arrangement described in this disclosure allows using lower force springs.

From the foregoing, it will be appreciated that specific embodiments of the arrangements described herein have been described for purposes of illustration, but that various modifications may be made without deviating from the scope of the invention. Accordingly, the invention is not limited except as by the appended claims.

What is claimed is:

1. A sealed cartridge containing a pressurized substance, comprising:

an elongated cylindrical body having a first end and a second end opposite the first end, wherein the first end includes an opening into an interior cavity of the elongated body;
a lid extending across the opening in the first end of the elongated body;
a flange at the first end of the elongated body that extends in a radial direction beyond the diameter of the body;
a coil spring disposed around the body, the coil spring being supported by the flange and biasing the body toward the first end, and
a rotating plate configured to, in a first state, support the flange to prevent axial movement between the flange and the rotating plate and, in a second state, allow the flange to move axially relative to the rotating plate;
wherein at least the first end is configured to open and release the pressurized substance.

2. The cartridge of claim 1 wherein the flange is integral with the lid.

3. The cartridge of claim 1 wherein the flange is integral with the body.

4. The cartridge of claim 1 wherein the flange is joined to the body by at least one of fastener, a thread, an adhesive, a weld, a solder, a press fit, a mechanical interference, and a retainer ring.

5. The cartridge of claim 1 wherein the flange is configured to prevent axial movement of the cartridge.

6. The cartridge of claim 1 wherein the body comprises:
a membrane joined to the body and sealing over the opening in a fluid tight fashion;
wherein the membrane is easier to pierce than the body and the lid.

7. The cartridge of claim 1 where in the flange comprises a ledge.

8. A sealed cartridge containing a pressurized substance, comprising:
a cylindrical body comprising:
a receptable
at least one lid joined in a fluid tight fashion to the receptacle; and
at least one opening in the body; and
a membrane joined to the body and sealing over the opening in a fluid tight fashion, wherein the membrane is a different material from the at least one lid;
a flange at a first end of the body that extends in a radial direction beyond a diameter of the body;
a coil spring disposed around the body, the coil spring being supported by the flange and biasing the body toward the first end; and
a rupturing member that is, in a first state, supported by the flange to prevent axial movement between the flange and the rupturing member and, in a second state, allow the flange to move axially relative to the rupturing member;
wherein at least the first end is configured to open and release the pressurized substance;
wherein the membrane is easier to pierce than the body.

9. The cartridge from claim 8, wherein the membrane is joined to the body by at least one of weld, point weld, laser weld, induction weld, friction weld, ultrasonic weld, glue, a seal, a crimp, a press fit, and soldering.

10. The cartridge of claim 8 wherein the body is made of at least one of a stainless steel, steel, metal alloys, and a plastic material.

11. The cartridge of claim 8, wherein the membrane is made of at least one of a stainless steel, steel, metal alloys, plastic, a film, a foil, and a laminated web.

* * * * *